US00PP29713P2

(12) United States Plant Patent
Van Dijk

(10) Patent No.: US PP29,713 P2
(45) Date of Patent: Sep. 25, 2018

(54) ***ANTHURIUM* PLANT NAMED 'ANTHESZJA'**

(50) Latin Name: ***Anthurium andraeanum* L.**
Varietal Denomination: ANTHESZJA

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,146

(22) Filed: Apr. 26, 2017

(51) Int. Cl.
*A01H 5/02* (2018.01)

(52) U.S. Cl.
USPC ..... Plt./366

(58) Field of Classification Search
USPC ..... Plt./366, 365
CPC ..... A01H 5/02; A01H 5/00; A01H 6/00
See application file for complete search history.

(56) References Cited

PUBLICATIONS

Upov Pluto Plant Variety Database Apr. 23, 2018 for *Anthurium* 'Antheszja', retrieved on Apr. 23, 2018, retrieved from the Internet at www.upov.int/pluto/en/index.jsp, one page. (Year: 2018).*
EU Community Plant Variety Rights Application No. 2015/2790, Application n° A201502440, filed Nov. 24, 2015, 8 pages.
EU Community Plant Variety Office Official Gazette, 1.2016, Feb. 15, 2016, cover page and pp. 28, 48.

* cited by examiner

*Primary Examiner* — June Hwu
(74) *Attorney, Agent, or Firm* — Jondle & Associates, P.C.

(57) ABSTRACT

A new *Anthurium* plant named 'ANTHESZJA' particularly distinguished by having small, shiny, white, ovate and very durable spathes that retain the original color for a very long period of time, dark green and long ovate, durable leaves, white spadix with light yellow-green tip, early and rich flowering continuously throughout the year and a plant height of 21.0 cm to 25.0 cm, is disclosed.

3 Drawing Sheets

Genus and species: *Anthurium andraeanum* L.
Variety denomination: 'ANTHESZJA'.

BACKGROUND OF THE NEW PLANT

The present invention comprises a new and distinct variety of *Anthurium*, botanically known as *Anthurium andraeanum* L., and hereinafter referred to by the variety name 'ANTHESZJA'. The new *Anthurium* plant is a product of a planned breeding program conducted by the inventor in Bleiswijk, the Netherlands. The objective of this breeding program was to create a new compact plant with small, shiny, white, ovate and durable spathes.

The new variety originated from a cross-pollination made in August 2008 in Bleiswijk, The Netherlands. The female parent is a red *Anthurium* pot plant designated '12461-07' (unpatented), and the male parent was a pink *Anthurium* pot plant designated '15580-01' (unpatented).

A single plant was selected from the progeny of the stated cross in June 2010 and has been asexually reproduced repeatedly by meristem tissue culture in Bleiswijk, The Netherlands over a 5-year period. The present invention has been found to retain its distinctive characteristics through successive asexual propagations.

Plant Breeder's Rights for this variety have been applied for in the European Union on Nov. 24, 2015. 'ANTHESZJA' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Small white spathe;
2) White spadix with a light yellow-green tip;
3) Green, long ovate leaves; and
4) Compact plant that develops many shoots.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 34-week old plant grown in a greenhouse in Bleiswijk, The Netherlands in January 2017. Colors in the photographs may differ from the color values cited in the detailed botanical description, which accurately describe the actual colors of the new variety.

DESCRIPTION OF THE NEW VARIETY

Figure 1:
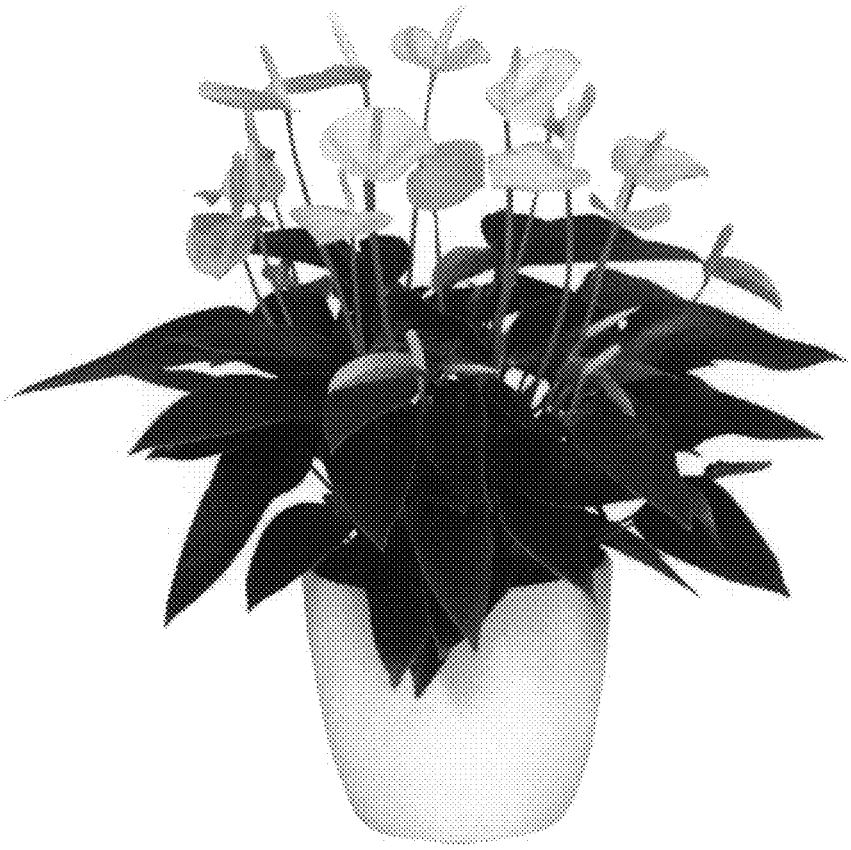
FIG. 1 shows the overall plant habit, including blooms, buds and foliage.
Figure 2:
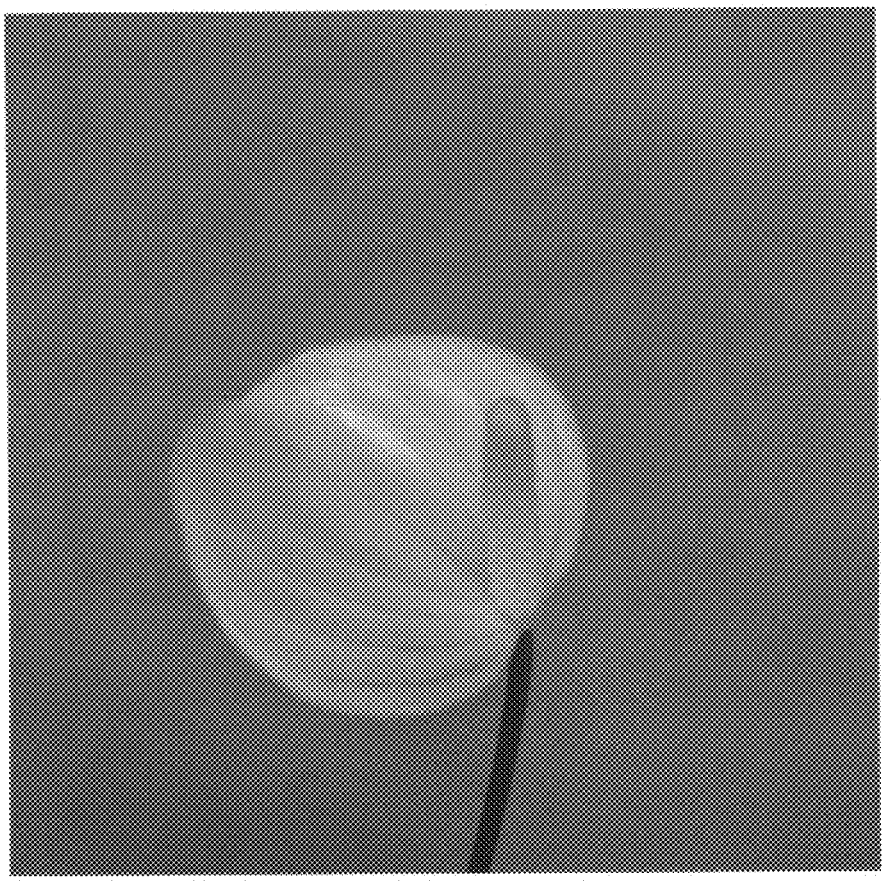
FIG. 2 shows a close-up of the mature spathe.
Figure 3:
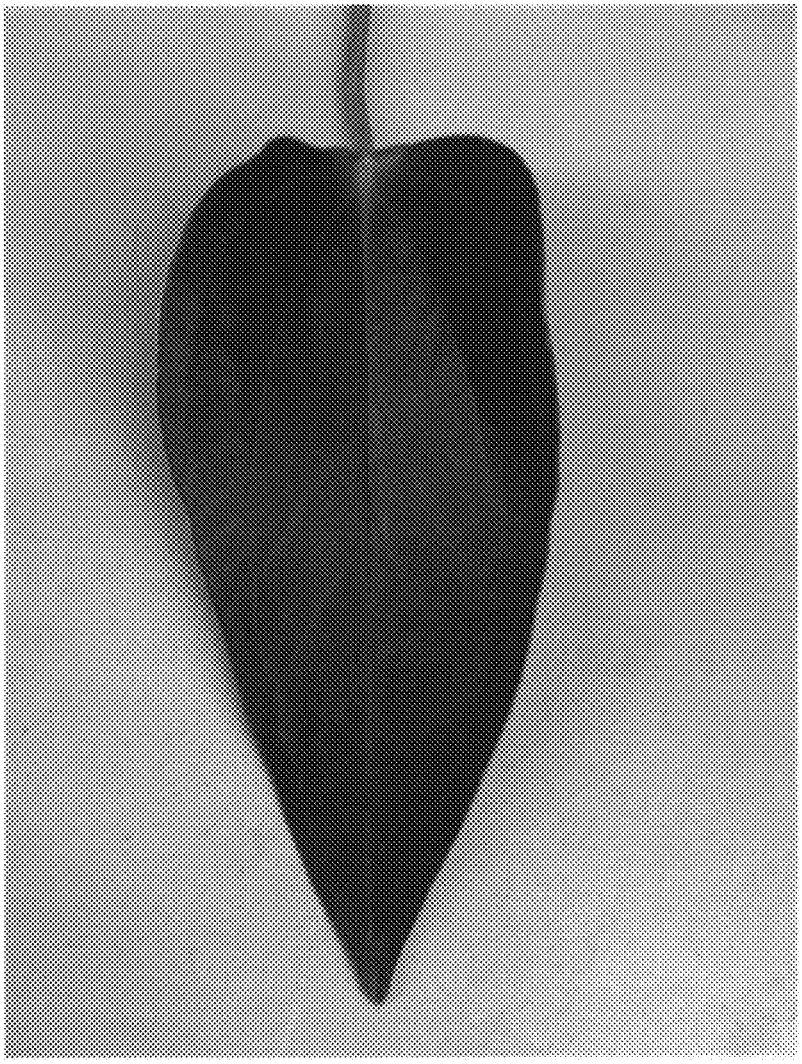
FIG. 3 shows a close-up of the upper leaf blade surface.

The following detailed description sets forth the distinctive characteristics of 'ANTHESZJA'. The data which define these characteristics were collected from asexual reproductions carried out in Bleiswijk, The Netherlands. The plant history was taken on 34-week old plants which were planted from tissue culture in 12-centimeter (diameter) pots and grown in a glass greenhouse between 19° C. and 24° C. Observations were made in January 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHESZJA'.

Parentage:

*Female parent*.—*Anthurium* plant '12461-07' (unpatented).

*Male parent*.—*Anthurium* plant '15580-01' (unpatented).

Plant:

*Propagation*.—Meristem tissue culture.

*Root description*.—Fleshy-creamy colored roots with small hairy lateral roots having yellow colored root tips.

*Time to produce a finished flowering plant*.—32 to 36 weeks after planting in a 12 cm (diameter) pot.

*Growth habit*.—Herbaceous perennial.

*Height* (*measured from soil, including inflorescence*).—21.0 cm to 25.0 cm.

*Width* (*measured from leaf tips*).—31.0 cm to 36.0 cm.

Leaves:

*Immature leaves*.—Length: 9.0 cm to 11.0 cm. Width: 5.0 cm to 6.0 cm. Color: Upper surface: RHS 146A. Lower surface: RHS 146B. Texture (both upper and lower surfaces): Shiny.

*Mature leaves*.—Length (fully expanded): 10.0 cm to 12.0 cm. Width: 6.0 cm to 7.0 cm. Shape: Long ovate. Apex: Acute. Base: Truncate. Leaf blade angle with the petiole: Between 135 degrees and 145 degrees. Leaf margin: Entire. Color: Upper surface: RHS 147A. Lower surface: RHS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146A. Lower surface: RHS 146B.

*Lobes*.—Absent.

*Petiole*.—Cross-section: Round. Diameter: 0.2 cm to 0.3 cm. Length: 6.0 cm to 8.0 cm for a mature leaf size. Color: Mature leaf: RHS 144A. Immature leaf: RHS 144B. Cataphyll color surrounding the petiole: Outside: RHS 144A. Inside: RHS 144C.

*Geniculum*.—Length: 1.6 cm to 1.9 cm. Width: 0.2 cm to 0.4 cm. Color: RHS 144A.

Inflorescence:

*Arrangement*.—Single.

*Flowering habit* (*length of flowering season*).—Continuous.

*Number of inflorescences per plant*.—18 to 25.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 80 degrees and 100 degrees; the spathe stands on a wiry peduncle about 2.0 cm to 3.0 cm above the foliage. The spathe is positioned far above the foliage.

*Shape*.—Ovate.

*Apex*.—Acuminate.

*Base*.—Ovate.

*Texture*.—Not blistered.

*Margin*.—Entire.

*Size*.—Length: 3.5 cm to 4.5 cm. Width: 3.5 cm to 4.5 cm.

*Lobes*.—Absent.

*Color*.—Just fully open: Upper surface: RHS NN155B. Lower surface: RHS NN155B. This white color remains for a very long period, at least more than 30 weeks after opening. After some weeks, the spathe turns green. Upper surface after some weeks: Light yellow-green (RHS 150D) with RHS144C over color. Lower surface after some weeks: Light yellow-green (RHS 150D) with RHS 144B over color.

Peduncle:

*Shape*.—Erect.

*Cross-section*.—Round.

*Length*.—13.0 cm to 15.0 cm.

*Diameter*.—0.2 cm to 0.3 cm.

*Color*.—RHS 144B.

Flowering time:

*General*.—One small rooted untreated tissue culture plant of 8.0 cm tall will flower, depending on season, after 32 to 34 weeks and 18 to 22 blossoms appear. More blossoms appear after some additional weeks so that a full flowering and commercial plant will have 18 to 25 white spathes. Smaller blossoms may occur on immature plants.

Spadix:

*Size*.—Length: 2.5 cm to 3.5 cm (depending on flower size). Width (at apex): 0.3 cm to 0.4 cm. Width (at base): 0.4 cm to 0.5 cm.

*Shape*.—Columnar.

*Angle from spadix tip to peduncle*.—160 degrees to 180 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 1D. Mature: RHS NN155A. Ages to: RHS NN155A.

Flowers:

*Quantity per spadix*.—70 to 100.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

Disease and pest resistance: No specific resistance or susceptibility observed to pathogens and pests common to *Anthurium*.

COMPARISON WITH PARENTAL AND COMMERCIAL VARIETIES

'ANTHESZJA' differs from the female parent plant '12461-07' (unpatented) in that 'ANTHESZJA' has white spathes and a white (RHS NN155A) spadix with light yellow-green (RHS 1D) tips, whereas '12461-07' has red spathes and a white (RHS NN155A) spadix with yellow (RHS 3B) tips. Additionally, 'ANTHESZJA' has unblistered spathes, whereas '12461-07' has blistered spathes.

'ANTHESZJA' differs from the male parent plant '15580-01' (unpatented) in that 'ANTHESZJA' has white spathes and a white (RHS NN155A) spadix with light yellow-green (RHS 1D) tips, whereas '15580-01' has red-pink spathes and a reddish (RHS 37C) spadix with reddish (RHS 37A) tips.

'ANTHESZJA' differs from similar commercial variety 'ANTHDOMAQ' (unpatented) in that 'ANTHESZJA' has ovate, unblistered spathes, whereas 'ANTHDOMAQ' has broad cordate, blistered spathes. Additionally, 'ANTHESZJA' has narrower spathes than 'ANTHDOMAQ'.

'ANTHESZJA' differs from similar commercial variety 'ANTHEFAQYR' (U.S. Plant Pat. No. 15,050) in that 'ANTHESZJA' ovate spathes, and long ovate shaped leaves, whereas 'ANTHEFAQYR' has cordate spathes, and deltoid shaped leaves. Additionally, 'ANTHESZJA' has narrower spathes than 'ANTHEFAQYR'.

I claim:

1. A new and distinct variety of *Anthurium* plant named 'ANTHESZJA', substantially as illustrated and described herein.

* * * * *